(12) United States Patent
Jensen et al.

(10) Patent No.: US 6,504,607 B2
(45) Date of Patent: *Jan. 7, 2003

(54) LIGHT SOURCE POWER MODULATION FOR USE WITH CHEMICAL AND BIOCHEMICAL ANALYSIS

(75) Inventors: Morten J. Jensen, San Francisco, CA (US); Patrick Kaltenbach, Bischweier (DE); Volker Brombacher, Pfinztal (DE)

(73) Assignees: Caliper Technologies, Corp., Mountain View, CA (US); Agilent Technologies Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/004,689

(22) Filed: Dec. 4, 2001

(65) Prior Publication Data

US 2002/0041375 A1 Apr. 11, 2002

Related U.S. Application Data

(63) Continuation of application No. 09/377,891, filed on Aug. 19, 1999, now Pat. No. 6,353,475
(60) Provisional application No. 60/143,399, filed on Jul. 12, 1999.

(51) Int. Cl.[7] .................................................. G01J 3/30
(52) U.S. Cl. ....................... 356/318; 356/320; 356/323; 356/324
(58) Field of Search ............................... 356/318, 319, 356/320, 323, 324, 244, 344; 250/458.1, 461.2

(56) References Cited

U.S. PATENT DOCUMENTS

| | | | |
|---|---|---|---|
| 4,930,893 A | | 6/1990 | Manian ........................ 356/344 |
| 5,026,159 A | * | 6/1991 | Allen et al. ................ 250/458.1 |
| 5,171,534 A | | 12/1992 | Smith et al. .............. 422/82.05 |
| 5,202,560 A | | 4/1993 | Koch et al. .................. 250/238 |
| 5,203,992 A | | 4/1993 | Drouen ..................... 210/198.2 |
| 5,300,779 A | | 4/1994 | Hillman et al. ............. 250/341 |
| 5,346,603 A | | 9/1994 | Middendorf et al. ........ 204/299 |
| 5,500,071 A | | 3/1996 | Kaltenbach et al. ..... 156/272.8 |
| 5,568,400 A | | 10/1996 | Stark et al. .................. 364/498 |
| 5,627,643 A | | 5/1997 | Birnbaum et al. .......... 356/344 |
| 5,641,400 A | | 6/1997 | Kaltenbach et al. ...... 210/198.2 |
| 5,699,157 A | | 12/1997 | Parce ......................... 356/344 |
| 5,736,410 A | | 4/1998 | Zarling et al. .............. 356/244 |
| 5,774,213 A | * | 6/1998 | Trebino et al. ............. 356/320 |
| 5,891,656 A | | 4/1999 | Zarlang et al. ............. 435/792 |
| 6,353,475 B1 | * | 3/2002 | Jensen et al. ............ 250/458.1 |

FOREIGN PATENT DOCUMENTS

EP 0 710 831 A1 5/1996

OTHER PUBLICATIONS

Legendre B L Jr et al.: "Ultrasensitive near–infrared laser––induced flourescence detection in capillary electrophoresis using a diode laser and avalanche photodiode". Journal of Chromatography A, NL, Elsevier Science, vol. 779, No. 1–2, Aug. 29, 1997 pp. 185–194.

* cited by examiner

Primary Examiner—Frank G. Font
Assistant Examiner—Roy M. Punnoose
(74) Attorney, Agent, or Firm—Ritter, Lang & Kaplan LLP

(57) ABSTRACT

Systems and methods for analyzing a sample are disclosed. The system may include a light source operable to transmit light onto the sample, a detector operable to detect intensity of the light emitted from the sample, and a power modulator. The power modulator modulates the light source power such that light is emitted from the light source in more than one mode to reduce changes in the emitted light due to temperature changes in the light source.

12 Claims, 4 Drawing Sheets

LIGHT SOURCE POWER MODULATION FOR USE WITH CHEMICAL AND BIOCHEMICAL ANALYSIS

RELATED APPLICATION

This is a Continuation of application Ser. No. 09/377,891, filed Aug. 19, 1999, now U.S. Pat. No. 6,353,475 B1, which is incorporated by reference.

The present application claims the benefit of U.S. Provisional Application Serial No. 60/143,399, filed Jul. 12, 1999.

BACKGROUND OF THE INVENTION

The present invention relates generally to chemical and biochemical analysis, and more particularly, to systems and methods for performing chemical and biochemical analyses of a sample within a microfluidic device.

Analysis of chemical and biochemical samples often requires detection and identification of the constituent elements of the sample. Microfluidic devices are often used to separate and control movement of the elements of the sample to detect a property of the elements with a detection system. The microfluidic devices typically include multiple wells that are interconnected with microchannels for transport of the sample. Application of a voltage across the channels permits the electrophoretic migration of macromolecular species in the sample. The samples often include an intercalating dye that becomes more fluorescent upon binding to the species of the sample. The fluorescent dyes are used to identify and locate a variety of cell structures such as specific chromosomes within a DNA sequence.

A variety of devices have been designed to read fluorescent labeled samples. In general the devices include at least one light source emitting light at one or more excitation wavelengths and a detector for detecting one or more fluorescent wavelengths. The light source is often a laser that emits light at one narrow center wavelength (single mode laser). For example, the laser may be optimized to operate at a single wavelength of 640 nm at full power, as shown in FIG. 1. However, as the temperature of the drive current of the laser changes, the wavelength typically changes. For example, when the laser is first turned on, the operating wavelength of the laser will increase as the laser warms up. If these wavelength changes were to occur as smooth transitions, the effect on the system could be minimized by warming up the laser prior to use or correcting the output of the laser to compensate for a slow wavelength drift.

Instead of smooth transition, the wavelength changes due to variations in temperature and drive current occur at sharp transitions or steps, as shown in FIG. 2. These abrupt wavelength changes are often referred to as laser mode hops and may result in spikes in the output data, because the optical detection system will behave differently at different emission wavelengths, due to the optical components, the reference detector, the chemical sample and the light source that often have slightly different attenuation or coupling at different wavelengths. This can lead to misidentification of the samples. The laser mode hops may even occur after a laser has warmed up if the system stabilizes at a temperature near a mode hop where slight variations in temperature will cause a sharp change in wavelength. Furthermore, the laser mode hops may affect detection system components which have characteristics dependent on the laser wavelength. The laser mode hops are difficult to correct for and may cause detection errors, particularly in electrophoresis, DNA sequencing, or cell analysis which requires detection of small changes in signals.

There is, therefore, a need for techniques that reduce sudden changes in the emitted light source wavelength due to temperature variations in the light source.

SUMMARY OF THE INVENTION

The present invention provides methods and systems for analyzing samples. One method of the present invention generally includes positioning the sample within an optical path of a light source and providing power to the light source. The light source power is modulated such that light is emitted from the light source in more than one mode to reduce changes in the emitted light due to temperature changes in the light source. The method can also include detecting the intensity of light emitted from the sample upon exposure to the light source.

In one embodiment of the present invention, the system generally includes a light source operable to transmit light onto the sample and a detector operable to detect intensity of the light emitted from the sample. The system further includes a power modulator operable to modulate the light source power such that light is emitted from the light source in more than one mode to reduce changes in the emitted light due to temperature changes in the light source.

In another embodiment, the system includes a microfluidic device for holding the sample and positioning the sample in an optical path of the light source.

The above is a brief description of some features and advantages of the present invention. Other features, advantages, and embodiments of the invention will be apparent to those skilled in the art from the following description, drawings, and claims.

BRIEF DESCRIPTION OF THE DRAWINGS

Corresponding reference characters indicate corresponding parts throughout the several views of the drawings.

DETAILED DESCRIPTION OF THE INVENTION

In the description that follows, the present invention will be described in reference to embodiments that analyze chemical and biochemical samples. More specifically, the embodiments will be described in reference to a system for use with a microfluidic device containing samples with fluorescent dyes used to identify cell structures, for example. However, the invention is not limited to use with samples containing a fluorescent label or microfluidic devices. Therefore, the description of the embodiments that follows is for purposes of illustration and not limitation.

Figure 3:
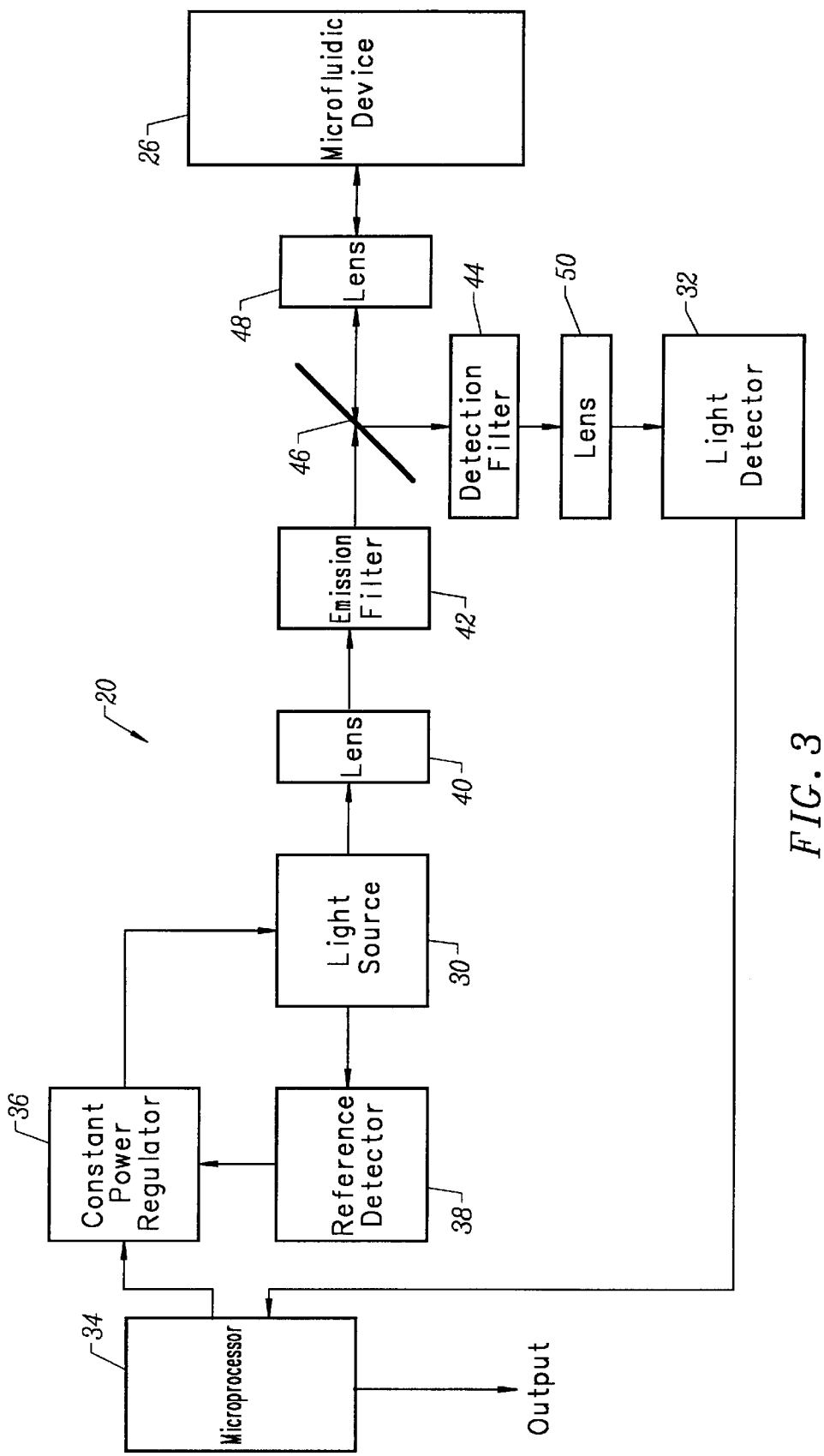
FIG. 3 is a block diagram of an embodiment of a detection system of the present invention.

Referring now to the drawings, and first to FIG. 3, a detection system 20 of the present invention is shown. Detection system 20 is used in the detection of light-based signals from analytical systems employing optical detection in microscale fluidic channels of a microfluidic device 26 (see FIG. 4). Examples of these systems are fused silica capillary systems (for capillary electrophoretic (CE) analysis) and microfluidic devices and systems which incorporate microscale channels. Such systems are generally described in U.S. patent application Ser. No. 08/845,754, filed Apr. 25, 1997 and Published International Patent Application Nos. WO 98/49548 and WO 98/00231, each of which is incorporated herein by reference in its entirety. Although described in terms of microfluidic systems, the present invention is applicable to a variety of types of laser diode analyses including multiwell plate assays, for example.

Figure 4:
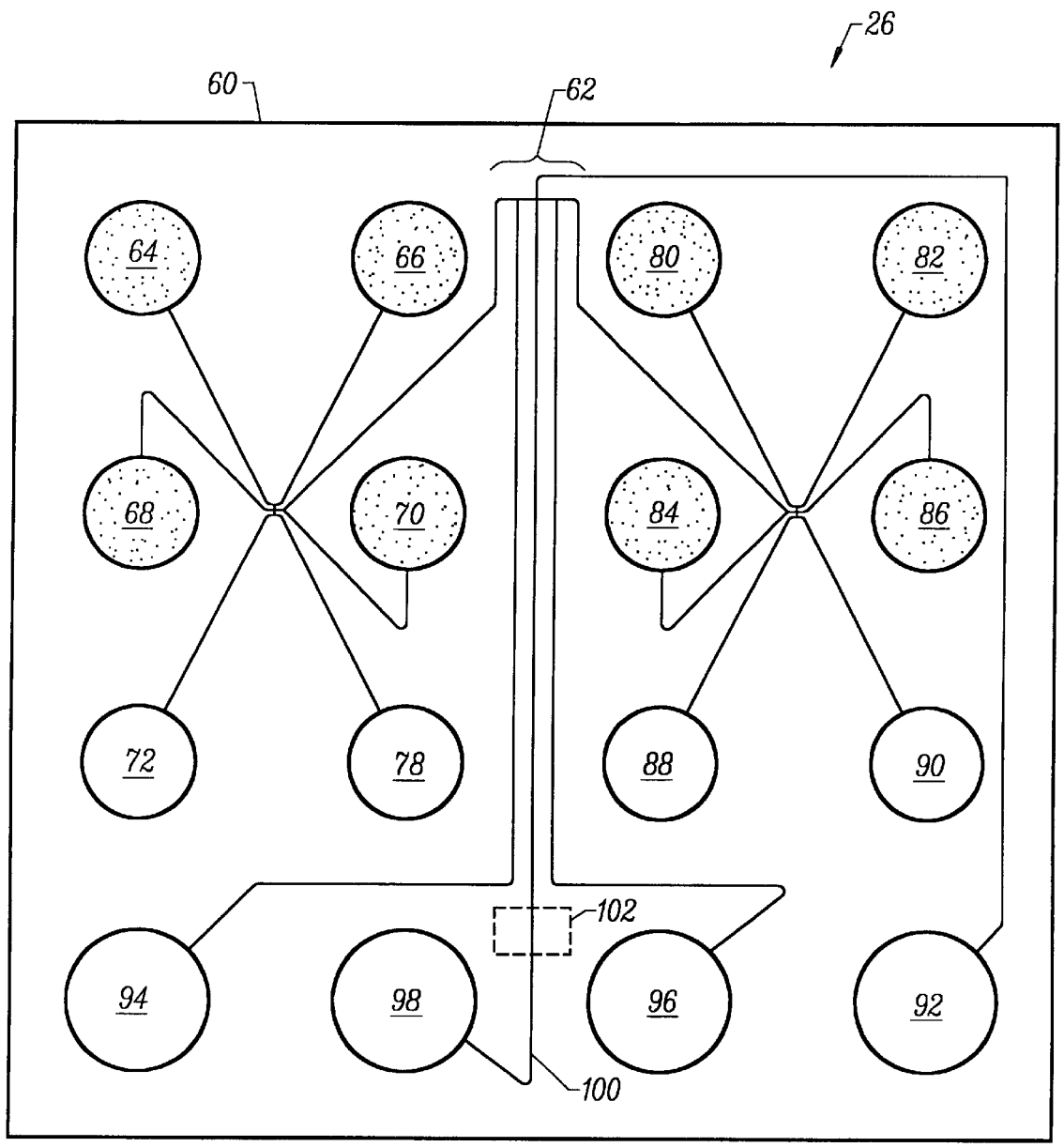
FIG. 4 is a schematic of a microfluidic device for use with the detection system of FIG. 3.

Now referring to FIG. 4, the channels of the microfluidic device 26 are adapted to handle small volumes of fluid. In a typical embodiment, the channel is a tube, groove, or conduit having at least one subsection with a cross-sectional dimension of between about 0.1 $\mu$m and 500 $\mu$m, and typically less than 100 $\mu$m. The channel is typically closed over a significant portion of its length. In operation, materials which are being analyzed are transported along the microscale fluid channels, past a detection region 102, where a detectable signal indicative of the presence or absence of some material or condition is measured by detection system 20. The signals within these channels result from the presence of light emitting substances therein. The light emitting substances may be fluorescent or chemiluminescent materials, for example, which are used as indicators of the presence or absence of some material or condition. Detection system 20 is used to measure the amount of light emitted from the fluorescent or chemiluminescent material within the channels of a reaction vessel. The reaction vessel may be microfluidic device 26, or any other suitable device such as a test tube, capillary tube, microchannel, or well in a multiwell plate, for example.

The magnitude of signal available for detection within the channels is typically extremely small due to the small dimensions of the microscale channels. For example, the power levels of signals from detection region 102 in the microfluidic channel are typically on the order of about 0.1 pW to about 10 pW. As further described below, detection system 20 of the present invention, controls the power input to the excitation light emitting source to prevent sharp changes in the wavelength of the excitation light emitted, to improve the accuracy of the output data. An example of microfluidic device 26 for use with detection system 20 is described in further detail below, following a description of the detection system.

FIG. 3 shows a block diagram of an embodiment of detection system 20 of the present invention. Detection system 20 may be used to detect fluorescence induced by exposure to laser radiation to generate chromatographic data, for example. As shown, detection system 20 includes a light source (e.g., laser diode) 30 for emitting light towards a sample located within microfluidic device 26, a light detector (e.g., fluorescent detector) 32 operable to detect light emitted from the sample and to convert the light into electric signals, and a microprocessor 34 for controlling the light source, decoding the electric impulses provided by the detector, and transmitting the decoded impulses to a host computer (not shown) as data. As described below, detection system 20 also includes a number of optical components including lenses, filters, and a beamsplitter, for filtering light and directing the excitation light emitted from the light source 30 towards the sample, separating fluorescence light emitted from the sample from reflected excitation light and directing it towards the light detector 32.

Microfluidic device 26 is positioned within detection system 20 with its detection region 102 (see FIG. 4) disposed in an optical path of light source 30 so that the system is in sensory communication with a channel of the microfluidic device via an optical detection window disposed across the channel of the microfluidic device at the detection region. The light source 30 is positioned at an appropriate distance for activating the fluorescent indicator within the test sample. As the sample passes the detection region 102, signals produced by the sample materials are detected by detector 32 and sent to microprocessor 34.

The light source 30 preferably produces light at an appropriate wavelength for activating fluorescently labeled samples. For example, a red laser diode may be used as the light source in order to facilitate detection of fluorescent species that excite in the red range. Light source 30 may be any number of light sources that provide the appropriate wavelength, including lasers, laser diodes, light emitting diodes (LED), and the like. Also, light source 30 may be configured to produce a wavelength suitable for detecting materials other than those that are fluorescently labeled. In one embodiment, light source 30 has a maximum optical power output of 10 mW and a visible wavelength of 634 nm, and is driven at a frequency of 100 kHz to 200 kHz. Light source 30 may be an InGaAsP laser diode available from Hitachi of Tokyo, Japan, under product designation HL6320G, for example.

Figure 1:
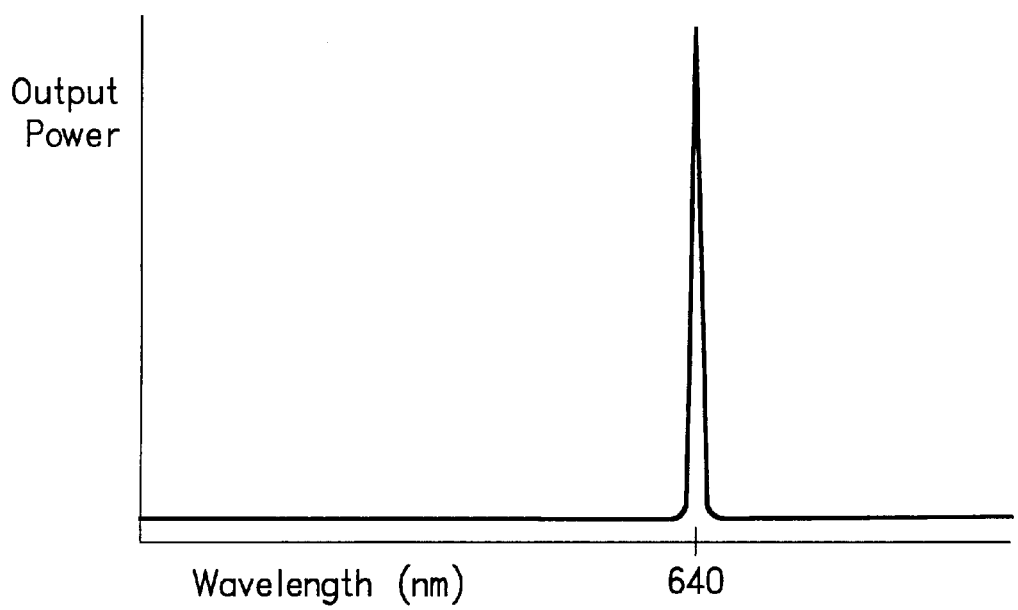
FIG. 1 illustrates a stabilized wavelength emitted from a laser diode.
Figure 2:
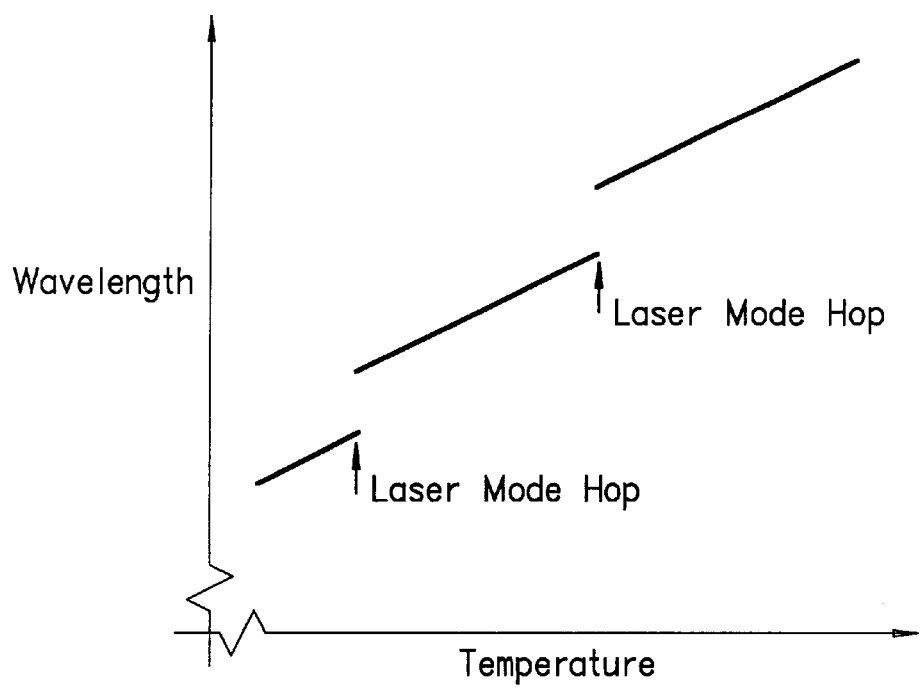
FIG. 2 illustrates variations in wavelength due to temperature changes.
Figure 5:
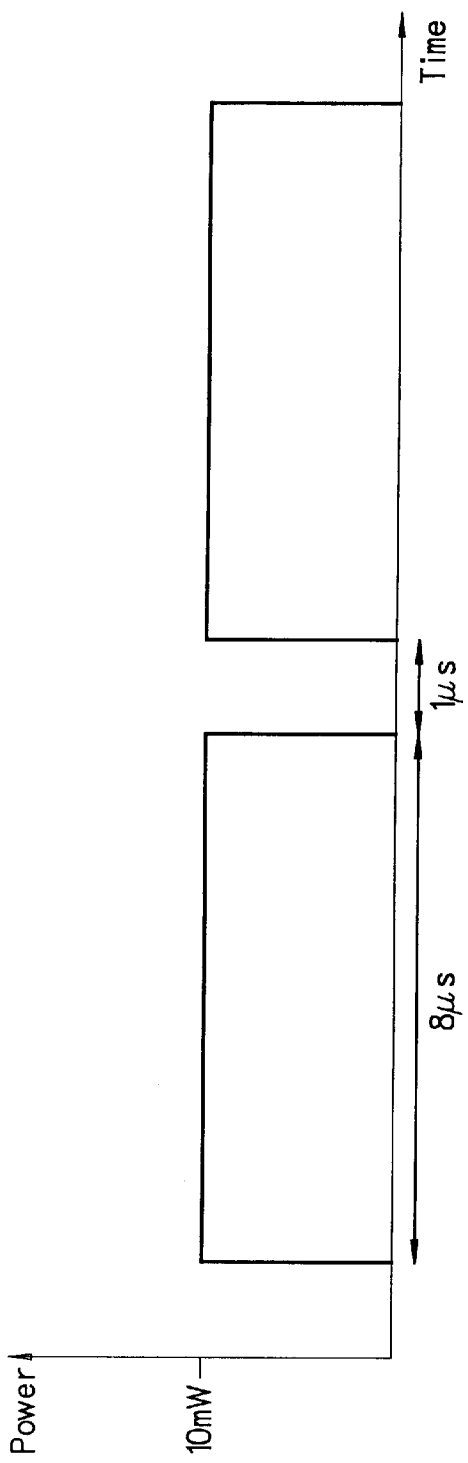
FIG. 5 illustrates a power timing cycle of the detection system of FIG. 3.
Figure 6:
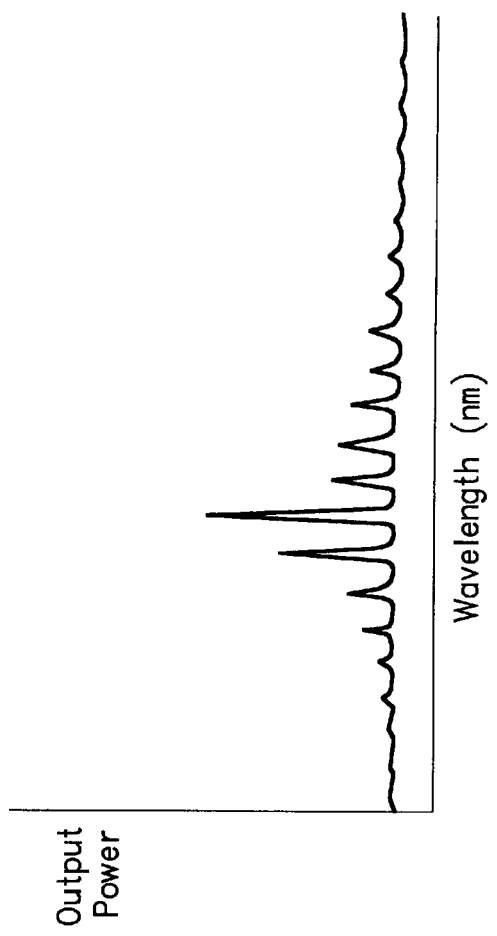
FIG. 6 illustrates variations in the wavelength of light emitted from a laser of the detection system with the power cycle shown in FIG. 5.

Light source 30 is controlled by the microprocessor 34 through a constant power regulator 36. Microprocessor 34 controls a power modulator in order to modulate the power of light source 30 as shown in FIG. 5. The power modulator cycles the power to light source 30 (e.g., on and off) to prevent the output of the light source from stabilizing at its center output, as shown in FIG. 1 and previously described. The cycling of light source 30 power forces the internal temperature of the light source to change which forces the light emission to shift permanently between different modes. Instead of stabilizing at a single wavelength output, the light output moves through several different wavelengths or modes as shown in FIG. 6. Since the output occurs over several modes, the output wavelength will change from one mode to the next and changes in wavelength due to temperature changes will no longer appear as a sharp transition.

In a preferred embodiment, the power is cycled on for eight microseconds and off for one microsecond (i.e., 111 kHz modulation frequency with an 89% duty cycle) to prevent the laser from reaching its stabilized output wavelength while limiting the decrease in power due to the off time (see FIG. 5). In another embodiment the power is turned on for approximately 50% of a cycle. The power may also be turned on for approximately 80% of a cycle. It is to be understood that the power cycle may be different than described herein without departing from the scope of the invention. For example, rather than cycling the power between zero and full power, the power may be cycled between 50% power and full power, or any other levels between zero and full power. Light source 30 may also be modulated using triangular, sawtooth, or sine wave modulation. The frequency of the laser modulation is preferably high compared to the output frequency of detector 32 to minimize undesirable coupling of modulation frequency to the output signal.

In order to remove effects of the modulated power input to the light source 30 on the output signal, electronic filtering is preferably provided to filter the signal output from light detector 32 so that the power modulation frequency does not appear in the output signal. Another option is to synchronize the laser modulation signal with the detector sampling time by synchronizing the respective clocks to eliminate traces of the laser modulation in the output signal.

When light source 30 is cycled on by microprocessor 34, constant power regulator 36 regulates power provided to the light source 30 to maintain a generally constant output power level. Constant power regulator 36 preferably includes a capacitor for averaging the optical laser power to provide a generally constant power output of 8 mW, for example. Constant power regulator 36 may be a laser diode driver available from IC-Haus of Bodenheim Germany, under product designation iC-Wj or iC-WJZ, for example.

Constant power regulator 36 receives input from a reference detector 38 which monitors the output power of the light source 30. The reference detector receives a portion of the light (e.g., 10%) output from the light source 30 and provides a current signal indicative of the output to the constant power regulator 36. Constant power regulator 36 uses the signal from reference detector 38 as feedback and adjusts the power of the light source 30 as required to maintain a generally constant output. The reference detector 38 and light source 30 may be provided together in a single package (e.g., HL6320G described above), for example.

Light emitted from the light source 30 passes through a lens 40 which focuses the light, and then through an emission filter 42. Emission filter 42 removes light with undesired wavelengths from the light source's emission band, primarily passing the wavelengths necessary to excite the selected flourchromes. For example, emission filter 42 may only allow light having a wavelength between 625 nm and 645 nm to pass therethrough.

After the light passes through emission filter 42, a portion of the light passes through a beamsplitter 46 mounted at a 45 degree angle of incidence to the incoming laser beam. Beamsplitter 46 passes the wavelengths necessary to excite the selected fluorochromes while reflecting the undesirable wavelengths. For example, beamsplitter 46 further filters the light emitted from the light source 30 by permitting only light with a wavelength less than 670 mn to pass therethrough.

The light that passes through beamsplitter 46 impinges on the sample within microfluidic device 26. A lens 48 is provided to focus the beam from the beamsplitter onto the sample. The fluorescence emitted from the sample travels back along the same optical path from the sample to beamsplitter 46 and is reflected by the beamsplitter towards light detector 32. The beamsplitter filters the light by reflecting the fluorescence light while allowing the excitation light to pass therethrough. A dichroic coating is preferably placed on a surface of the beamsplitter 46 to filter the reflected excitation light from the fluorescence light. Beamsplitter 46 first directs the fluorescence light to a detection filter 44 which further filters the signal emitted from the sample. Detection filter 44 may be configured to allow only light having a wavelength between 665 nm and 705 nm to pass through, for example. The emission and detection filters 42, 44 may be filters available from Omega Optical, Inc., of Brattleboro, Vt., for example. A focusing lens 50 is disposed adjacent detection filter 44 to direct the light reflected from beamsplitter 46 into light detector 32.

Light detector 32 converts the incoming light into electric impulses. These electric impulses are decoded by microprocessor 34 and sent to the host computer as data. Detection system 20 is preferably coupled to the host computer via a serial data connection, for transmitting detected light data to the computer for analysis, storage, and data manipulation.

Light detector 32 may be a photodiode, avalanche photodiode, photomultiplier tube, diode array, or imaging systems, such as charged coupled devices (CCDs), and the like. Light detector 32 may include, for example, an integrator and an analog-to-digital converter having an analog input coupled to an output of the integrator, as described in U.S. patent application Ser. No. 09/104,813, filed Jun. 25, 1998 which is incorporated herein by reference.

Light detection system 20 described above is for use with a microfluidic device containing a sample with a fluorescent label. It is to be understood that the system may be used to detect other types of labels including light absorbing labels.

FIG. 4 shows one embodiment of a microfluidic device 26 which can be used with the detection system 20 of the present invention. Microfluidic device 26 includes a body structure 60 having an integrated channel network 62 disposed therein. Body structure 60 includes a plurality of reservoirs 64–90 for holding reagents, sample materials, and the like. Also included is a buffer reservoir 92 and waste reservoirs 94, 96, and 98. The reagents or samples are transported from their respective reservoirs, either separately or together with other reagents from other reservoirs into a main channel 100 and along the main channel to the waste reservoir 98, past detection region (or window) 102. Detection window 102 is preferably transparent so that it is capable of transmitting an optical signal from the channel over which it is disposed. Detection window 102 may merely be a region of a transparent cover layer, e.g., where the cover layer is glass or quartz, or a transparent polymer material, e.g., PMMA, polycarbonate, etc. Alternatively, where opaque substrates are used in manufacturing microfluidic device 26, transparent detection windows fabricated from the above materials may be separately manufactured into the device.

Microfluidic device 26 preferably includes at least two intersecting channels and may include three or more intersecting channels disposed within single body structure 60. Channel intersections may exist in a number of formats, including cross intersections, "T" intersections, or any number of other structures whereby two channels are in fluid communication. Microfluidic device 26 may have multiple sample introduction ports or reservoirs, for the parallel or serial introduction and analysis of multiple samples. Alternatively, microfluidic device 26 may be coupled to a sample introduction port, e.g., a pipetor, which serially introduces multiple samples into the device for analysis.

The samples may be transported along main channel 100 and past detection window 102 by application of external vacuum or pressure, or use of capillary, hydrostatic, centrifugal, or gravity forces, or the application of electric fields such as with electrokinetic transport systems, or combinations of the above, for example. The electrokinetic transport system directs materials along the interconnected channels through the application of electrical fields to the material, thereby causing material movement through and among the channels, i.e., cations will move toward the negative electrode, while anions will move toward the positive electrode.

Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electrostatic flow of fluid and material within a channel or chamber structure, which results from the application of an electric field across such structures. In brief, when a fluid is placed into a channel which has surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at or near the fluid/surface interface, or a positively charged sheath surrounding the bulk fluid in the channel. Application of a voltage gradient across the length of the channel will cause the proton sheath to move in the direction of the voltage drop, i.e., toward the negative electrode.

Microfluidic device 26 described herein is useful in performing a variety of analyses, such as electrophoretic separation of macromolecules (e.g., nucleic acids, proteins) and high throughput screening assays, e.g., in pharmaceutical discovery and diagnostics as disclosed in Published International Patent Application Nos. WO 98/49548 and WO 98/00231. It is to be understood that the microfluidic device used with detection system 20 of the present invention may be different than those described herein without departing from the scope of the invention.

While the above is a complete description of preferred embodiments of the invention, various alternatives, modifications, and equivalents can be used. It should be evident that the invention is equally applicable by making appropriate modifications to the embodiments described above. Therefore, the above description should not be taken as limiting the scope of the invention that is defined by the metes and bounds of the appended claims along with their full scope of equivalents.

What is claimed is:

1. A method of analyzing a sample comprising:

positioning the sample within an optical path of a light source;

cycling power to the light source;

detecting an intensity of light emitted from the sample with a detector upon exposure of the sample to the light source; and minimizing an effect of cycling power on an output signal of the detector.

2. The method of claim 1 wherein positioning the sample comprises positioning a microfluidic device containing the sample within the optical path.

3. The method of claim 2 wherein positioning the sample further comprises electrokinetically transporting the sample within the microfluidic device.

4. The method of claim 1 wherein cycling power comprises cycling power to the light source between an on and an off state whereby the light source is powered on for more than about 50% of the time.

5. The method of claim 1 wherein cycling power comprises cycling power to the light source between an on and an off state whereby the light source is powered on for more than about 80% of the time.

6. The method of claim 1 wherein cycling power comprises cycling power to the light source between a first power level greater than 0% power and a second power level less than 100% power.

7. The method of claim 1 wherein cycling power comprises cycling power to the light source between a first power level of about 50% power and a second power level of about 100% power.

8. The method of claim 1 wherein the light source is a laser.

9. The method of claim 1 wherein the light source is a laser diode.

10. The method of claim 1 wherein cycling power comprises cycling power to the light source between approximately zero milliwatts and ten milliwatts.

11. The method of claim 1 wherein minimizing an effect of cycling power on the output signal of the detector comprises filtering the output signal of the detector.

12. The method of claim 8 wherein minimizing an effect of cycling power on the output signal of the detector comprises synchronizing a laser modulation signal with a detector sampling time.

* * * * *